United States Patent [19]

Davies

[11] 4,207,351

[45] Jun. 10, 1980

[54] WATER REMOVAL BY HYDRATE FORMATION

[75] Inventor: Thomas M. C. Davies, Cuxton, England

[73] Assignee: British Vinegars, London, England

[21] Appl. No.: 802,862

[22] Filed: Jun. 2, 1977

Related U.S. Application Data

[63] Continuation-in-part of Ser. No. 716,950, Aug. 23, 1976, abandoned.

[30] Foreign Application Priority Data

Sep. 5, 1975 [GB] United Kingdom ............... 36629/75
May 26, 1977 [GB] United Kingdom ............... 22282/77

[51] Int. Cl.$^2$ .............................................. A23L 2/38
[52] U.S. Cl. ...................................... 426/387; 62/534; 426/524; 210/22 R
[58] Field of Search .................... 210/22, 21, 22 R, 71; 426/17, 384, 524, 386, 387; 62/4, 10, 12, 20, 533, 534, 535; 260/676 H

[56] References Cited

U.S. PATENT DOCUMENTS

| | | | |
|---|---|---|---|
| 1,941,951 | 1/1931 | Muller | 62/533 |
| 2,410,583 | 11/1946 | Hutchinson | 260/676 H |
| 2,904,511 | 9/1959 | Donath | 62/533 |
| 3,027,320 | 3/1962 | Buchanan | 62/533 |
| 3,079,761 | 3/1963 | Toulmin | 62/533 |
| 3,126,334 | 3/1964 | Harlow | 62/533 |
| 3,216,833 | 11/1965 | McKay | 426/524 |
| 3,216,930 | 11/1965 | Glew | 210/22 |
| 3,243,966 | 4/1966 | Glew | 62/4 |
| 3,266,263 | 8/1966 | Pollock | 62/533 |
| 3,415,747 | 12/1968 | Glew | 62/533 |
| 3,856,492 | 12/1974 | Klass | 62/533 |

FOREIGN PATENT DOCUMENTS

| | | | |
|---|---|---|---|
| 699083 | 12/1964 | Canada | 426/384 |
| 1024447 | 3/1966 | United Kingdom | 62/535 |

OTHER PUBLICATIONS

Chemical Engineer Handbook (Perry's), McGraw-Hill, New York, 4th Edition, 17-26-28.
1964 Saline Water Conservation Report, U.S. Dept. of Interior, Office of Saline Water, pp. 188-194.
First International Symposium on Water Desalination, Oct. 3-9, 1965, The Koppers Hydrate Process, Peter van der Heem, U.S.A. pp. 1-11.
Chemical Engineer Handbook (Perry's), McGraw Hill, New York, 4th Edition 17-24.
The Condensed Chemical Dictionary, Eighth Edition, Van Nostrand Reinhold, New York, 1971, p. 887.

*Primary Examiner*—Charles N. Hart
*Assistant Examiner*—Ernest G. Therkorn
*Attorney, Agent, or Firm*—Diller, Ramik & Wight

[57] ABSTRACT

A process for removing water from an aqueous solution. A hydrate forming fluid is contacted with an aqueous solution at a temperature below the maximum temperature at which said hydrate forming fluid forms a solid hydrate in the presence of said solution and at a temperature at which there is precipitation of solid solute and/or of the concentrated solution remaining after hydrate formation so as to form a magma comprising solid hydrate, any unreacted hydrate forming fluid and any unreacted aqueous solution. The hydrate forming fluid and at least part of the water constituent of the solid hydrate are separated from the solute by fractional sublimation, evaporating and/or elution to produce a substantially hydrate forming fluid-free product comprising said solute and any remaining water.

52 Claims, No Drawings

WATER REMOVAL BY HYDRATE FORMATION

This application is a continuation-in-part of Ser. No. 716,950, filed Aug. 23, 1976, now abandoned.

This invention relates to the removal of water from aqueous solutions.

It has previously been known that solid hydrates may be formed between certain hydrate forming fluids and water from aqueous solutions such as sea water and that after separation of the solid hydrate by filtration or similar mechanical handling processes, pure water may be obtained from the separated hydrate by decomposition thereof. However, in the case of solutions wherein the solute solidifies at the temperatures used to form the solid hydrate, techniques such as filtration cannot be used to separate the solid hydrate from the remainder of the mixture.

Accordingly it is an object of the present invention to provide a process for the removal of water from aqueous solutions of the type in which a solid hydrate is formed wherein the solid hydrate is separated from the solid phase, preferably by non-mechanical means.

The present invention provides a process for removing water from an aqueous solution which comprises:

(a) contacting an aqueous solution with a hydrate forming fluid at a temperature below the maximum temperature at which said hydrate forming fluid forms a solid hydrate in the presence of the solution, and at a temperature at which there is precipitation of solid solute and/or of the concentrated solution remaining after hydrate formation, so as to form a magma comprising solid hydrate, solid solute, any unreacted hydrate former and any unreacted aqueous solution; and (b) separating
  (i) the hydrate former and at least part of the aqueous constituents of the solid hydrate, and
  (ii) at least part of the solute, from each other, by fractional sublimation, evaporation and/or elution, so as to produce a substantially hydrate former-free product comprising the solute and any remaining water.

In a preferred separation process, the solid mixture resulting from the treatment of the aqueous solution with hydrate forming fluid is subjected to temperature and pressure conditions that result in the breakdown of the solid hydrate to ice and hydrate former, the hydrate former is removed by vacuum evaporation, and the mixture of ice and solid solute is preferably separated by differential or fractional sublimation.

In the case where the solute is acetic acid and the hydrate forming fluid is trichlorofluoromethane (also known under the Trade Mark Freon 11 but hereinafter referred to as TCFM), recovery of the excess former and decomposition of the hydrate former is usually effected at about 0° C. since the TCFM hydrate is very stable at lower temperatures.

Breakdown of the hydrate to give ice and gaseous hydrate former may be conveniently effected at 0° C. and 5 mm Hg. The gaseous hydrate former separated off in this way also contains the solute as a vapour which may be removed by condensing the hydrate former—solute mixture and then distilling off the hydrate former to leave solute alone. The ice may then be selectively sublimed off from the remaining magma at, for example, 0° C. and 4.5 mm Hg to yield a residue comprising, in the case of vinegar, non-volatile minor vinegar constituents and those constituents with triple points below that of water.

Other suitable temperature-pressure combinations may readily be determined by trial and error and/or by the use of vapour pressure data at various temperatures to select conditions under which at the chosen temperature the vapour pressure of the ice exceeds that of the chosen pressure whilst the vapour pressure of the solute is less than the chosen pressure and vice versa. If difficulty is experienced in selecting suitable conditions, for example, when the solute has a similar triple point to water, high yields can be obtained by passing the vapours through a column of water vapour absorbing material such as silica gel or anhydrous copper sulphate (which can be regenerated) the non aqueous vapour being collected.

In a further aspect the present invention provides a process for removing water from an aqueous solution which comprises:

(a) contacting an aqueous solution with a hydrate forming fluid at a temperature below the maximum temperature at which said hydrate forming fluid forms a solid hydrate in the presence of the solution and above the maximum temperature at which ice forms in the aqueous solution so that said hydrate forming fluid forms a solid hydrate with water from the aqueous solution; and (b) decomposing the solid hydrate so as to produce hydrate former and ice, and then separating at least part of the ice and at least part of the solute, from each other, by fractional sublimation of the mixture, so as to produce a substantially hydrate former-free product comprising solute and any remaining water.

As used herein the term "sublimation" is a process wherein a solid is converted directly into a vapour and includes such processes wherein the clathrate hydrate is decomposed without passing through a liquid phase into hydrate former gas and water vapour or ice.

Another separation process is differential elution using a solvent or solvents in which the solute is soluble but in which the solid hydrate of the hydrate fluid used is substantially insoluble at the temperatures at which the hydrate is formed and is stable, or vice versa i.e. in which the solute is insoluble and the solid hydrate soluble. In the case where the solute is acetic acid suitable elution solvents for the solute include, ethanol, formaldehyde and butanol.

A preferred method of differential elution is when the magma of solid hydrate and solid solute is separated from the liquid component which may contain one or more of unreacted former, unreacted aqueous solution, and unreacting minor constituents that may be present in the solution being concentrated. The latter fraction may be distilled to recover any such minor constituents that may be present, as for example, in the case of vinegar, and any dissolved solute.

Although the minor constituents also comprise solutes of the aqueous solution from which water is being removed they will be referred to herein as the minor constituents whilst the major constituent(s), will be referred to herein as the solute, for convenience.

The solid phase is then rapidly dried by evaporation of the unseparated former and then by increasing the vacuum (i.e. decreasing pressure) the solid hydrate becomes unstable and is broken down to ice and former. The former is at once evaporated and may be collected for recycling. This leaves a mixture of ice and solid solute. The ice will start to melt at below 0° C. due to the depression of the freezing point by the solute solution. However if the solute is highly soluble in water at this temperature it is possible to obtain a significant degree of concentration if the solute is dissolved and the solution removed prior to the ice all melting. The unmelted ice recovered then represents the amount of water extracted from the original solution. An alternative method is to treat the ice/solid solute mixture before much melting occurs with a solvent which gives rapid solution of the solute but little effect on the ice (examples are T.C.F.M. or Methylene dichloride when the solute is acetic acid). The solution is then separated from the ice by filtration and the solute recovered by evaporation.

In a particularly advantageous form of the process of the present invention, separation is effected by fractional sublimation comprising the steps of:

(a) selective sublimation or evaporation of the solid solute and any remaining concentrated solution; and (b) recovery of the sublimed or evaporated solute.

Where the volatility of the hydrate former is greater than that of the solid solute and its concentrated solutions, the process conveniently includes the preliminary step of removal of any excess hydrate former by selective evaporation usually preceded by draining.

In certain cases, as for example in the case of a process for the concentration of aqueous acetic acid, the solid solute may be partially or entirely in the form of a solid concentrated solution and in this case it is the solid solution of solute that is selectively sublimed and then recovered. In other cases the concentrated solution may be liquid and in these cases it is this solution that is evaporated followed by sublimation of any solid solute remaining.

In the particular case of vinegar and aqueous acetic acid solutions it has been found that addition of excess hydrate former to the solution under hydrate forming conditions with the temperature below about 2° C. and at atmospheric pressure, results in a very rapid reaction in which solid hydrate is formed under the amount of water that has reacted is such that the remaining aqueous acetic acid solution has a concentration of the order of 85–90% w/v at which point the said solution solidifies to produce a solid aqueous acetic acid solution. It will be appreciated that further hydrate formation will no longer be possible, even though unreacted hydrate former may remain, since the water "trapped" in the solid solution will not be available to react with the excess unreacted hydrate former. Some of the solute that was dissolved in the hydrate former prior to reaction is precipitated as solute alone during or after precipitation of the solid concentration solution.

At this stage the magma will therefore comprise solid hydrate, solid solute, a solid aqueous solution of solute, and any excess unreacted hydrate former. Since the hydrate former will usually be a relatively volatile substance, it may be readily removed by selective evaporation. Thus, for example, where the hydrate former is TCFM it may be readily removed selectively by vacuum evaporation at a pressure of 20 mm.Hg. at 0° C. It will be appreciated by those skilled in the art that other temperature/pressure combinations may be used, provided that the temperature does not exceed the melting point of about 2° C. at atmospheric pressure of the solid solution. A particular advantage of using TCFM as the hydrate former for this process is that hydrate formation may be readily carried out at atmospheric pressure at readily attainable temperatures with consequent production economies.

If the temperature of the reaction medium during hydrate formation with TCFM or DCFM at atmospheric pressure is over about 2° C. or if, after hydrate formation, the temperature is allowed to rise to over about 2° C. some or all of the residual aqueous acetic acid solution may remain in the liquid state, and therefore available to react with any excess hydrate former present. Nevertheless, there is little further hydrate formation due to the instability of the hydrate under these conditions in concentrated acetic acid solutions.

When a TCFM hydrate has been formed the temperature and pressure conditions for selective sublimation of the solid solution, i.e. conditions under which the solid solution is substantially sublimed whilst the solid hydrate is substantially not decomposed into its constituent parts nor sublimed, may be readily determined by those skilled in the art by conventional means. In the case of a TCFM hydrate and solid concentrated aqueous acetic acid, the latter may be easily selectively sublimed and thus separated from the TCFM hydrate at a temperature below about 0° C. at a reduced pressure for example at −29° C. under a pressure of 0.5 mm Hg. Again, it will be appreciated that the sublimation conditions may be varied by increasing both pressure and temperature or by reducing both temperature and pressure.

The TCFM hydrate is quite stable and at lower temperatures it does not break down at the reduced pressures. In the case of DCFM, though, a less stable hydrate is formed. This may be broken down at about 100 mm Hg. at 0° C. The water can be substantially recovered from the remaining magma by applying a vacuum providing the triple point of solute is not passed i.e. temperatures above and pressures below the triple point are not used.

When the concentrated aqueous solution is liquid the hydrate is not very stable. Recovery of the solute can then be achieved by merely applying a slight vacuum, but high yields can also be obtained by aeration at atmospheric pressure or slightly above atmospheric pressure e.g. up to 50 p.s.i. or 4 atmospheres, at temperatures of about 2°–5° C. It will also be appreciated by those skilled in the art that increasing the pressure will increase the stability of the hydrate and thus higher temperatures can be used for the recovery of the solute.

By "Aeration" is meant herein the contacting of a stream of relatively quickly moving inert gas such as air conveniently at from 0 to 100 meters per second, for example, at about 2 meters per second, with the magma. Desirably the air stream is directed through the magma so as to maximise the rate of removal of the solute from the magma.

It will be appreciated by those skilled in the art that this aeration process affords considerable production economies in that it avoids the need for costly means for producing and maintaining low pressures whilst allowing the process to be carried out at temperatures as close to ambient as possible—thereby also reducing the amount of refrigeration required. The use of aeration also makes it convenient to use a slightly higher pressure at any given temperature to increase the stability of the solid hydrate whilst still allowing vaporisation of the solute or concentrated solution to continue. Thus aeration can be conveniently used at temperatures above 5° C. i.e. with the magma substantially liquid if above atmospheric pressures are used.

In addition the aeration procedure can also, if desired, be used to effect a degree of temperature control of the magma by varying the temperature of the air or other inert gas used.

The air or other inert gas, after passing through the magma, is passed through a condensing unit and the solute or solute concentrate recovered.

Aeration can also be used with a substantially solid magma provided this is first broken down into small particles to allow the ready passage of the aeration gas through the magma whilst at the same time increasing the surface area of the magma in contact with the aeration gas.

When the solid and/or liquid solution has been sublimed and/or evaporation it will be appreciated that the solute may be recovered from any former that has also condensed due to breakdown of the hydrate. Part or all of any water that is found in the vapour before condensation may be removed so that the solute may be recovered in the form of relatively pure solute if required. For example, part or all of the sublimed water may be removed by passing the sublimed vapours over a dehydrating agent such as anhydrous silica gel prior to condensation.

In the case of vinegar, as has already been mentioned hereinbefore, there are, in addition to the acetic acid solute, also present in aqueous solution various minor constituents which contribute to the flavour and aroma of the vinegar. These include on the one hand non-volatile constituents such as acetate salts and salts of other organic acids which are in-soluble in TCFM and others which are soluble in TCFM and on the other hand volatile constituents such as acetaldehyde and ethanol.

Where excess TCFM (or DCFM) is used for hydrate formation the unreacted former remaining after completion of hydrate formation may be drained off together with the former-soluble non-volatile constituents and some of the volatile constituents which are dissolved in the excess former, and retained. The drained off former may then be added to the condensed former and concentrated acetic acid obtained by selective sublimation and/or evaporation of the magma. This mixture will already contain the remaining volatile micro-constituents not dissolved in the excess former. The mixture may then be selectively evaporated to distill off the former to yield concentrated acetic acid containing the former-soluble minor constituents and the other volatile micro-constituents i.e. a vinegar concentrate deficient in some of the minor non-volatile constituents. Nevertheless for practical purposes such a vinegar concentrate will in most cases be quite acceptable.

If desired, though, all the non-volatile minor constituents not recovered from the excess former may be recovered by breaking down any remaining hydrate and subliming and/or evaporating off the ice and/or water as well as evaporating off any remaining TCFM to yield a residue comprising said non-volatile minor constituents which may then be recombined with the vinegar concentrate.

It will, of course, be appreciated that the amount of hydrate former-soluble micro-constituents extracted in the hydrate former can vary depending on factors such as the contact time between the hydrate former and the vinegar before hydrate formation is completed and that if desired, the amount of these micro-constituents can be maximised by increasing the contact time.

Although TCFM is a particularly valuable hydrate forming fluid, especially for use with aqueous acetic acid solutions, on account of its non-toxicity, commercial availability, low cost and ease of handling due to the fact that it is a liquid at ambient temperatures and pressures hence avoiding the need for costly pressurised storage and reaction vessels and due to the fact that it can form a solid clathrate hydrate at ambient pressures when the temperature is sufficiently reduced, other hydrate forming fluids may also be used. Known hydrate forming fluids together with their hydrate formulae are shown in Table 1 wherein M represents any of the individual hydrate forming molecules in the given section.

TABLE 1

| Hydrate Formula | Hydrate Former M |
| --- | --- |
| M. 5.75 . $H_2O$ | $A, Kr, N_2, O_2, H_2S, H_2Se, CO_2$ |
| | $N_2O, PH_3, Ash_3, CH_3F, CH_3Cl, CH_4$ |
| M. 5.75 $H_2O$ or M. 7.66 $H_2O$ | $SO_2, CH_2F_2, C_2H_2, C_2H_4$ |
| M. 7.00 $H_2O$ | $Xe, Br_2, NF_2, CHF_3, CF_4, CH_3Br$ |
| | $C_2H_3F, CH_3CHF_2, C_2H_6$ |
| M. 17 $H_2O$ | $CH_2Cl_2, CHCl_3, CCl_4, CH_3I, C_2H_5Cl$ |
| | $CH_3CF_3, CH_3CHCl_2, CHBrF_2, CClF_3$ |
| | $CCl_2F_2, CBr_2F_2, CBrClF_2$ |
| | $CF_3I, C_3H_6, C_3H_8,$ cyclo $C_5H_{10}$ |

The selection of operating conditions for formulation of the solid hydrate are well known and understood in the art. Briefly the actual operating conditions for a given system are based on the pressure-temperature equilibrium line data for a given hydrate former as predetermined and calculated for a desired solution concentration, operating temperature and pressure limit utilising the formula:

$$P_{1t^o} = (P_o/x^n)_{t^o}$$

where:

$t^o$ = preselected temperature of operation for formation of the solid hydrate and the concentrated aqueous solution.

$P_1$ = minimum absolute pressure of the hydrate former to be exerted at temperature $t^o$ to achieve the desired final concentration of the aqueous solution through solid hydrate formation.

$P_o$ = absolute pressure of the hydrate former to be exerted at temperature $t^o$ to achieve formation of solid hydrate with pure water.

(Assumes water is saturated with hydrate former, but contains substantially no other solute).

x = mole fraction of water at desired final concentration of the concentrated aqueous solution.

n = number of water molecules associated with one molecule of hydrate former in the solid gas hydrate.

The values of $P_o$ at a preselected $t^o$ can be obtained from experimental and published data.

Although ordinarily the formula will be utilized to determine the operating pressure ($P_1$) for a preselected temperature ($t^o$), known pressure ($P_o$) of formation of solid hydrate with pure water and for a desired final solution concentration as represented by residual mole fraction of water (x) in the solution, generally it is to be understood that if any two of the operating variables, i.e. $P_1$, $P_f$, and x at a preselected $t^o$ are known, the third can be found by valculation using the above formula.

In the case where TCFM is used to remove water from acetic acid solutions it has been found that hydrate formation proceeds rapidly and substantially complete reaction of the water to form solid hydrate can be obtained up to an acetic acid concentration of about 85 to 90% w/v when an excess of TCFM over the stoichiometrically required amount under atmospheric pressure provided a sufficiently low temperature, preferably below 5° C., is used.

The selection of the hydrate forming fluid will depend on various factors such as safety, cost and availability but is primarily determined by the particular solute which it is desired to concentrate and its properties as well as on the process selected for the separation of the solute concentrate from the hydrate or vice versa. Thus in general the hydrate forming fluid is chosen for maximising ease of the separation process, subject to the other abovementioned criteria, for example where decomposition of the hydrate with simultaneous differential sublimation is employed the hydrate forming fluid is chosen to provide a solid hydrate which can be readily broken down and whose constituents are easily separable from the solute. Where differential sublimation is carried so as to selectively vapourise the solute or solid solution then the hydrate former can be chosen so as to provide a hydrate which is substantially not decomposed under the conditions used to selectively vapourise the solute or solid solution. When the conditions used are such that the hydrate does decompose then, providing the triple point of water is not passed, this does not affect the basic process. In practice during the beginning of sublimation at 0° to −10° C. there is some breakdown. As the heat required for vapourisation comes from the magma there is a reduction in the temperature thereof with a consequent increase in stability of the hydrate. In practice the temperature of the magma may fall to as low as −29° C. by the end of the vapourisation. In the case of aqueous acetic solutions where the separation process involves differential sublimation, especially suitable hydrate forming fluids other than TCFM include dichloromethane, trichloromethane and dichlorofluoromethane.

The amount of hydrate forming fluid used in the initial solid hydrate formation stage of the process of the invention may be varied within broad limits. Desirably though the amount used will be at least an amount that is sufficient to react with all the water present in the solution to be concentrated though advantageously an excess of the hydrate former is used especially when vinegar is to be concentrated since in that case the minor constituents of the vinegar (which contribute to its flavour and character) may be conveniently recovered in the excess unreacted hydrate former (at least to some extent).

In practice the reaction of hydrate formers, such as TCFM with water to form solid hydrates, is substantially stoichiometric so that the required amount of hydrate former may be readily calculated. However, as has already been noted in the case of acetic acid solutions, in certain cases not all the water present may be available to react with the hydrate former.

Thus in the case where the hydrate former is TCFM the amount of TCFM required is at least 1 molecule of TCFM for every 17 molecules of water i.e. at least about 1 part of TCFM to 2 parts of vinegar by weight. Conveniently approximately equal parts of vinegar and TCFM, by volume, are used.

The above processes of the present invention have been found to be especially valuable for the concentration of vinegar. Vinegar is essentially an aqueous acetic acid solution with an acetic acid content of the order of 5 to 10% w/v depending on its source and method of manufacture which solution contains small amounts of various other natural products constituents which contribute to the flavour of the particular vinegar. Particular vinegars that may be mentioned include distilled malt vinegar, alcohol (spirit) vinegar, grain vinegar, wine vinegar, cider vinegar and flavoured vinegars. Malt vinegar in England usually contains at least 4% w/v acetic acid and wine vinegar in France and Italy is required to contain at least 6 and at least 7% w/v acetic acid, respectively.

From the above it will be apparent that in general vinegars comprise some 90-95% w/v of water. It is therefore clearly desirable that if vinegar transportation costs are to be significantly reduced, the vinegar should be substantially concentrated. On the other hand it must be borne in mind that many of the minor natural products constituents of vinegar which are essential to the flavour of the vinegar are susceptible to denaturation at elevated temperatures and under other severe conditions.

It is therefore a further object of the present invention to provide a process for the concentration of vinegar which process does not substantially denature the vinegar constituents or result in any substantial loss of the vinegar constituents—other than the water.

Accordingly in a further aspect the present invention provides a process for producing a vinegar concentrate by removing water from vinegar comprising (a) contacting the vinegar with a hydrate forming fluid at a temperature below the maximum temperature at which said hydrate forming fluid forms a solid hydrate in the presence of the vinegar and at a temperature at which there is precipitation of at least one of solid acetic acid and solid aqueous acetic acid solution remaining after solid hydrate formation, so as to form a magma comprising solid hydrate at least one of solid acetic acid and solid aqueous acetic acid solution, any unreacted hydrate former, any unreacted aqueous vinegar solution, and minor vinegar constituents; and (b) separating
(i) the hydrate former and at least part of the aqueous constituents of the solid hydrate and any unreacted hydrate former, and
(ii) at least part of the acetic acid, from each other, so as to produce a substantially hydrate former-free acetic acid concentrate, and where the minor vinegar constituents are not separated with the acetic acid concentrate; recovering at least part of the minor vinegar constituents and recombining them with the acetic acid concentrate, so as to produce a vinegar concentrate.

A particularly preferred hydrate forming fluid for use in this process is trichlorofluoromethane.

The solid hydrate may be separated from the concentrated vinegar and any solid acetic acid that has precipitated out the vinegar solution, by sublimation or solution of solid hydrate, with or without decomposition thereof, under temperature and pressure conditions at which any solid acetic acid is substantially not vapourised. Preferably though separation is effected by selective vapourisation of the acetic acid or acetic acid solution under conditions such that the solid hydrate remains substantially undecomposed.

Some of the minor constituents and some solute may be dissolved in the excess hydrate former. These may be conveniently separated from the magma by draining and may then be recovered by distilling off the hydrate former present, and after collecting they may be recombined with the solute concentrate obtained after completion of the concentration process (providing the required final concentration).

Of course, if the resulting product is acceptable for a given end use, then no attempt may be made to recover microconstituents, and the vinegar concentrate obtained will in this case only contain such microconstituents as may be present in the concentrated acetic acid solution recovered.

It will of course, be appreciated that where the highest degrees of concentration are required it may be necessary or more convenient to carry out the concentration in more than one step i.e. by repeating the concentration process one or more times. The extent to which this is possible may, however, be limited by the conditions necessary for hydrate formation. Thus, for example, difficulty may be experienced in forming hydrates with partially concentrated solutions such as acetic acid solutions, containing 30% w/v or more of acetic acid. In this case where any minor constituents have been separated from the solute (e.g. in solution in excess hydrate former), they need not be recombined with the concentrated aqueous solution of the solute until the final concentration cycle has been completed.

The degree of concentration obtainable by the process of the present invention will depend on various factors such as the nature of the solute and of the hydrate former used, the particular separation process used and the number of concentration cycles carried out. Nevertheless concentrations of 40%, 60% or even 80% w/v acetic acid may be achieved by the selection of suitable conditions in the case of vinegar concentration by a process of the present invention, the concentrated vinegar being, after reconstitution with water, substantially indistinguishable, for practical purposes, from untreated vinegar.

EXAMPLE 1

Concentration of aqueous acetic acid

A. Solid hydrate formation

To aqueous acetic acid solution (1 liter of 10% w/v) was added liquid trichlorofluoromethane (TCFM, 1 liter) and the mixture cooled to 3° C. Vigorous agitation together with external cooling and internal cooling, by the addition of solid carbon dioxide, was then carried out so as to ensure that the temperature of the mixture remained below 5° C. throughout the hydration formation step. After a few minutes a magma comprising unused TCFM, solid acetic acid, residual aqueous acetic acid and solid hydrate, was obtained.

B. Separation of Hydrate

The magma was subjected to vacuum evaporation (3 mm Hg at 0° C.) for 60 minutes until no more hydrate sublimed. The unused TCFM was first removed by this step and was subsequently recovered together with the TCFM trapped in the hydrate. The removal of the TCFM and later removal of the hydrate reduces the temperature to 0° C. and this temperature is maintained thereafter by suitable heat application for rapid TCFM removal. This process yielded a mixture of solid glacial acetic acid and residual aqueous acetic acid which at ambient temperatures gave 82% w/v aqueous acetic acid solution.

EXAMPLE 2

Concentration of malt vinegar

A. Solid Hydrate Formation

Liquid trichlorofluoromethane (TCFM, 500 ml) was added to malt vinegar (500 ml.) and the mixture stirred vigorously for 3 minutes at 3° C. Excess TCFM and other liquids were then drained off from the solid hydrate and acetic acid which were then divided into two equal parts.

B. Separation of Hydrate (1) One part of the solids was subjected to vacuum evaporation (3.4 mm Hg at −0.5° C.) until no more TCFM or water was removed. This step yielded aqueous acetic acid solution containing 69% w/v acetic acid.

(2) The other part of the solids was homogenised with a little ice cold water for 10 minutes in a cold room at −4° C. The liquid phase was then filtered off under vacuum. The remaining solids yielded under ambient condition an aqueous solution containing 42.5% w/v acetic acid.

The liquids from the first stage were then added, after removal of the TCFM from them by evaporation, to acetic acid solutions obtained after the separation of the hydrate to finally yield concentrated malt vinegar.

EXAMPLE 3

Concentration of Spirit Vinegar

A. Solid Hydrate Formation

Liquid trichlorofluoromethane (TCFM, 250 ml) was added to spirit vinegar (250 ml.) and the mixture stirred vigorously for 3 minutes at 3° C. Excess TCFM and other liquids were then strained off from the solid hydrate and acetic acid.

B. Separation of Hydrate

The solids resulting from the first stage were subjected to vacuum evaporation (10 mm Hg at −5° C.) until no more TCFM came off. The pressure was then reduced to 3 mm Hg and the temperature increased to −1° C. Initially ethanol and acetaldehyde were removed and collected. Evaporation was then continued until no more water could be removed. This process yielded a residue which at ambient temperatures gave an aqueous solution containing 68% w/v acetic acid.

To the aqueous acetic solutions were then added the recovered ethanol and acetaldehyde and the liquids from the first stage after the TCFM has been evaporated from them, finally yielding concentrated spirit vinegar.

EXAMPLE 4

Concentration of Spirit Vinegar

Solid Hydrate Formation (a) 50 ml. of Spirit Vinegar was added to 50 ml. of TCFM and the mixture attemperated at 0° C. and agitated with an air bleed until most or all the aqueous phase had reacted. The excess TCFM was then drained off and stored for recovery of solutes. The solid magma was similarly stored at 0° C. until required for evaporation and sublimation.

(b) A second method of clathrate hydrate formation was used: to 100 ml. of spirit vinegar at 0° C., 75 ml of TCFM was added dripwise over a period of 6 hours. The temperature was maintained at 0° C. and agitation was achieved by an air bleed. After 6 hours the excess TCFM and dissolved constituents were filtered off from the solid magma constituents and stored until required for recovery of solutes. The solid magma was stored at 0° C. until required for evaporation and sublimation.

Separation of Hydrate

The solid magmas from hydrate formations (a) and (b) were placed in a freeze dryer and a vacuum applied. The excess former was initially removed and the vacuum was then increased until the clathrate hydrate decomposed and the former was released. The temperature was maintained just below 0° C. by infra red radiation. As the hydrate decomposes, ice and gaseous TCFM are formed. The TCFM was condensed for later re-use. After a substantial part of the former was removed the thin layer of magma consisted of ice crystals and solid acetic acid. The pressure was now reduced so as to sublime the ice (3 mm. Hg at 0° C.), leaving a substantial portion of the acetic acid which allowed to regain room temperature at normal atmospheric pressure.

The excess TCFM from the clathrate formation stage was carefully distilled at 20° C. until all traces of TCFM were removed as shown by G.L.C. examination of the product. Hydrate formation method (b) gave higher yields of dissolved acetic acid than method (a): after combining the distillates and the sublimed samples the former method yielded a concentrate with 84% w/v acetic acid and the latter gave a concentration of 89%.

EXAMPLE 5

A 100 ml. aliquot of Malt Vinegar was reacted with 100 mls. TCFM as in Example 4. The excess TCFM containing the minor constituents of the malt vinegar was drained from the solid magma and the dissolved acetic acid and minor constituents were recovered by distillation at 20° C. until no TCFM was detected by G.L.C. analysis of the residue.

The solid magma was then subjected to vacuum distillation under mild conditions until the excess TCFM was removed. The vacuum was then increased until the hydrate decomposed leaving solid acetic acid and ice. Some melting ice was observed at −1° C. and in addition to this 1 ml. of ice cold water was added. The slurry was agitated briefly and the liquid drained off by vacuum filtration. This liquid was concentrated acetic acid and when recombined with the solutes from the excess TCFM concentrated vinegar was obtained, the level of concentration of the acetic acid in the aqueous solution being governed by the amount of ice that had melted into the liquid eventually drained off from the slurry. After the addition of the TCFM dissolved acetic acid and minor constituents the acetic acid content of the samples was 54% w/v.

EXAMPLE 6

Hydrate formation was carried out as in Example 4(a). The solid magma was then subjected to an initially low vacuum to remove excess TCFM and then the hydrate was rapidly broken down to give ice and solid acetic acid. To the mixture of ice and acetic acid, at a recorded temperature of −4° C., an equal volume of TCFM, at 1° C., was added and the mixture agitated. The TCFM was then removed by filtration from the ice and liquid was evaporated at 20° C. until no more TCFM was detected. This method yielded after recombination with the minor constituents recovered from the distilled TCFM an acetic acid content of 89% w/v.

Analysis of reconstituted concentrated vinegars by gas liquid chromatography (G.L.C.) showed that the concentrated product resembled the original vinegar very closely. The compounds acetaldehyde and ethanol found in vinegar were determined individually and the remainder of the volatile constituents were grouped together. The determinations of quantity were based on the G.L.C. peak areas.

The following table gives the acetic acid content (% w/v) of and the percentages (by weight) of the minor constituents recovered in, five vinegar concentrates obtained by the method of Example 6 but carried out on a small scale using 10 ml. vinegar samples. The error in the minor constituent determinations is of the order of ±7 to 8%.

| Vinegar Type | Acetic Acid Conc. % w/v * | % Acet-aldehyde | % Ethanol | % Other volatiles |
| --- | --- | --- | --- | --- |
| Spirit | 67 | 94 | 89 | 93 |
| Wine | 71 | 64 | 76 | 77 |
| Wine (white) | 61 | 81 | 73 | 82 |
| Malt | 82 | 92 | 98 | 102 |
| Cider | 58 | 84 | 86 | 91 |

*The acetic acid concentrations given were determined by acid-base titration and include any minor acidic constituents recovered that may be present in the vinegar being concentrated.

EXAMPLE 7

500 ml of TCFM (trichlorofluoromethane) was vigorously agitated at 0° C. with an equal volume of spirit vinegar which had an acidity of 11.8% w/v. After the reaction the temperature had risen slightly and the temperature was reduced by immersing the flask in ice-cold water. The excess hydrate former was drained off as far as possible. This TCFM and the vinegar microconstituents and some dissolved solute present therein was stored at +4° C. in a sealed vessel.

The remaining excess hydrate former was then evaporated at 100 mm Hg and this caused the temperature to rapidly fall. When the excess hydrate former had all been removed it was stored at +4° C. together with that collected earlier. The temperature of the remaining magma was then reduced to −15° C. and the pressure reduced to 0.5 mm Hg. A bleed of air was introduced under the slab of magma (which under these conditions is a porous solid) to increase the rate of sublimation and the sublimate was collected and stored at 4° C. together with the previously collected hydrate former. The resulting mixture of hydrate former was then distilled until no further weight loss occurred i.e. until all the hydrate former had been removed, and yielded a residue of 62 mls of 87% w/v acetic acid.

The residual magma was left to reach room temperature in a sealed bottle and the TCFM remaining therein was then drained off from the bottom of the container for reuse.

EXAMPLE 8

500 ml of TCFM was vigorously agitated at 0° C. with an equal volume of spirit vinegar which had an acidity of 11.8% w/v i.e. a content of acetic and other acids equivalent to 11.8% w/v of acetic acid. After reaction the temperature had risen towards the desired 3.5°–4° C. The magma was then placed in a tube with a water jacket and it was maintained at 3.5°–4° C. Air was pumped into the base of the tube and this continued until no further distillate was obtained. After collection the distillate was redistilled at 20° C. to remove the hydrate former leaving a concentrated acetic acid solution comprising 43 ml of 83% w/v acetic acid.

The residual magma was left to reach room temperature in a sealed bottle and the TCFM was run off from the bottom of the container for reuse.

What is claimed is:

1. A process for removing water from an aqueous solution which comprises:
   (a) contacting an aqueous solution with a hydrate forming fluid at a temperature below the maximum temperature at which said hydrate forming fluid forms a solid hydrate in the presence of said solution, and at a temperature at which there is precipitation of solid solute and/or of the concentrated solution remaining after hydrate formation, so as to form a magma comprising at least two solid phases which are solid hydrate and solid solute, and at least one liquid phase which includes any unreacted hydrate forming fluid and any unreacted aqueous solution; and
   (b) separating from each other, by a fractionation process comprising one of fractional sublimation, fractional evaporation, and fractional elution while there are at least two solid phases in the magna:
      (i) the hydrate forming fluid constituent and at least part of the water constituent of said solid hydrate, and
      (ii) at least part of said solid solute; and
   (c) recovering a substantially hydrate forming fluid free product comprising the solute of said solid solute and any remaining water.

2. The process of claim 1 wherein the solid hydrate of solid magna is decomposed into ice and hydrate forming fluid by at least one of an increase in temperature and a reduction in pressure to provide temperature and pressure conditions at which said solid hydrate decomposes and at which the solid solute is substantially unaffected.

3. The process of claim 2 wherein the solid solute and at least part of the ice are separated from each other by fractional sublimation at temperature and pressure conditions such that one of the ice and the solid solute is volatilised.

4. The process of claim 2 wherein the solid solute and at least part of the ice are separated from each other by sublimation at temperature and pressure conditions, such that both the ice and solid solute are volatilised and then contacted with a water vapour absorbing material.

5. The process of claim 4 wherein the water vapour absorbing material is selected from silica gel and anhydrous copper sulphate.

6. The process of claim 2 wherein at least part of the ice is maintained in the solid state and the solid solute is mechanically separated from said ice in the solid state.

7. The process of claim 6 wherein part of the ice is allowed to melt to form liquid water in which at least part of said solid solute dissolves.

8. The process of claim 6 wherein liquid water is added in an amount substantially less than said at least part of the ice maintained in the solid state and at least part of said solid solute allowed to dissolve in said added liquid water.

9. The process of claim 2 wherein at least part of the ice is maintained in the solid state and a non-aqueous elution solvent, in which ice is substantially less soluble than is the solute, is added to form a solution of the solid solute, which solution is then mechanically separated from the solid ice, and the liquid solute is then recovered from said solution by separation from said elution solvent.

10. The process of claim 9 wherein when the solid solute is acetic acid, the non-aqueous solvent is selected from trichlorofluoromethane and methylene dichloride, and said acetic acid is separated from said elution solvent by evaporation of said non-aqueous elution solvent.

11. The process of claim 2 wherein when said solute is acetic acid, and said hydrate forming fluid is trichlorofluoromethane, said hydrate decomposition is carried out at a temperature not higher than 0° C. and a pressure not higher than about 750 mm of mercury so that said solid hydrate is decomposed and the trichlorofluoromethane volatilised whilst the acetic acid is maintained in substantially solid form.

12. The process of claim 11 wherein the hydrate decomposition is carried out at a temperature and pressure such that the hydrate is decomposed into ice and trichlorofluoromethane and that the ice is then fractionally sublimed off by reducing the pressure to a value not greater than 4.5 mm of mercury when a temperature of 0° C. is used.

13. The process of claim 12 wherein the ice is fractionally sublimed off at 3 mm of mercury and 0° C.

14. The process of claim 1 wherein the solid solute is separated from the solid hydrate by differential elution using a solvent in which the solid solute is substantially more soluble than is the solid hydrate.

15. The process of claim 14 wherein when the solid solute is acetic acid, the elution solvent is selected from ethanol, formaldehyde and butanol.

16. The process of claim 14 wherein when the solute is acetic acid the elution solvent is methylene chloride.

17. The process of claim 14 wherein when the solid solute is acetic acid the elution solvent is trichlorofluoromethane, at least part of said acetic acid being dissolved in said trichlorofluoromethane.

18. The process of claim 17 wherein the trichlorofluoromethane elution solvent containing dissolved acetic acid is separated from the solid hydrate by filtration.

19. The process of claim 18 wherein the trichlorofluoromethane elution solvent containing dissolved acetic acid obtained after filtration is subjected to fractional evaporation so as to produce trichlorofluoromethane vapour and acetic acid residue.

20. The process of claim 1 wherein the solid hydrate is decomposed into ice and hydrate forming fluid vapour by at least one of an increase in temperature and a reduction in pressure to provide temperature and pressure conditions at which said solid hydrate decomposes and at which the solid solute is substantially volatilized whilst the ice remains substantially in the solid phase, in the residual magma.

21. The process of claim 20 wherein the solid solute is acetic acid and the aqueous solution comprises vinegar comprising aqueous acetic acid containing volatile, non-volatile hydrate forming fluid—soluble, and non-volatile hydrate forming fluid—insoluble, minor constituents and wherein after the solid hydrate has been decomposed, and the solid solute recovered, the ice is removed from the residual magma to yield a residue comprising at least part of said hydrate forming fluids insoluble non-volatile, minor constituents.

22. The process of claim 21 wherein said hydrate forming fluid-insoluble minor constituents are recombined with the product comprising acetic acid, volatile microconstituents and any remaining water so as to yield a vinegar concentrate.

23. The process of claim 1 wherein at least the stoichiometric amount of hydrate forming fluid required to react with all the water in the aqueous solution, is used.

24. The process of claim 1 wherein the hydrate forming fluid is selected from dichloromethane, trichloromethane and dichlorofluoromethane.

25. The process of claim 1 wherein the hydrate forming fluid is trichlorofluoromethane.

26. The process of claim 25 wherein at least 1 mole of trichlorofluoromethane is used for every 17 moles of water in said aqueous solution from which the water is being removed.

27. The process of claim 25 wherein the hydrate formation is carried out at atmospheric pressure and at a temperature below 5° C.

28. The process of claim 1 wherein the hydrate forming fluid is used in an amount in excess of the amount required to react with all the water in the aqueous solution and wherein the liquid phase remaining after formation of said solid phases and containing excess unreacted hydrate forming fluid is filtered off from the solid phases and then evaporated to recover any minor constituents of the solution being concentrated which remain in the liquid phase during the solid hydrate formation, said minor constituents being recombined with the product recovered in step c.

29. A process for producing a vinegar concentrate by removing water from vinegar comprising:
(a) contacting the vinegar with a hydrate forming fluid at a temperature below the maximum temperature at which said hydrate forming fluid forms a solid hydrate in the presence of the vinegar and at a temperature at which there is precipitation of at least one of solid acetic acid and solid aqueous solution remaining after solid hydrate formation, so as to form a magma comprising solid hydrate, at least one of solid acetic acid and solid aqueous acetic acid solution, any unreacted hydrate forming fluid, any unreacted aqueous vinegar solution, and minor vinegar constituents; and
(b) separating at least part of said solid acetic acid and at least part of said minor vinegar constituents from said hydrate forming fluid and at least part of the water constituent of the solid hydrate so as to produce a vinegar concentrate substantially free of said hydrate forming fluid, the separating being effected by at least one of fractional sublimation, fractional evaporation and fractional elution while there are at least two solid phases present in the magma.

30. The process of claim 29 wherein:
(i) a first part of the magma comprising said hydrate forming fluid and at least part of the water constituent of the solid hydrate, any unreacted hydrate forming fluid, and at least part of the minor vinegar constituents, and a second part of the magma comprising at least part of the solid acetic acid, are separated from each other so as to produce an acetic acid concentrate comprising said at least part of the acetic acid;
(ii) said at least part of the minor vinegar constituents are separated from said first part of the magma, and
(iii) said minor vinegar constituents are recombined with said acetic acid concentrate so as to produce a vinegar concentrate.

31. The process of claim 30 wherein said first and second parts of the magma are separated by subjecting the magma to temperature and pressure conditions at which said solid hydrate decomposes and at which the hydrate forming fluid and solid acetic acid are substantially volatilised whilst said at least part of the water constituent of the solid hydrate is maintained in the solid state, the volatilised hydrate forming fluid and acetic acid are condensed to yield a condensate, and the condensate selectively evaporated to distill off the hydrate forming fluid and yield a residue comprising acetic acid.

32. The process of claim 31 wherein said at least part of the minor vinegar constituents are separated from said first part of the magma by selective volatilisation of said at least part of the water constituent of the solid hydrate and of any unreacted hydrate forming fluid.

33. The process of claim 32 wherein the condensate is combined with said at least part of the minor vinegar constituents prior to distilling off said hydrate forming fluid.

34. The process of claim 33 wherein the unreacted hydrate forming fluid is separated off from said first part of the magma prior to separating said first and second parts of the magma from each other and said separated off hydrate forming fluid is combined with the condensate prior to distilling off the hydrate forming fluid.

35. The process of claim 30 wherein the hydrate forming fluid is trichlorofluoromethane.

36. The process of claim 1 wherein separation of
(i) said hydrate forming fluid constituent and at least part of the water constituent of said solid hydrate, and
(ii) at least part of said solid solute, from each other, is effected by at least one of selective sublimation and evaporation of said solid solute and by recovery of said solid solute that has been sublimated and/or evaporated, under temperature and pressure conditions at which said solid hydrate is substantially not decomposed nor sublimated.

37. The process of claim 36 wherein said separation includes the preliminary step of selective evaporation of any excess unreacted hydrate forming fluid present in said magma.

38. The process of claim 36 wherein said separation is effected under temperature and pressure conditions such that a substantial part of the concentrated aqueous solution is present in the liquid state by passing a stream of inert gas through the magma.

39. The process of claim 38 wherein said inert gas is air.

40. The process of claim 39 wherein aeration is effected at a temperature of the magma above 5° C. at a pressure greater than atmospheric pressure.

41. The process of claim 38 wherein the stream of air is passed through the magma at a velocity of from 0.1 to 100 meters per second.

42. The process of claim 36 wherein when the solid solute is present in the form of a solid concentrated aqueous solution of the solute, said separation is effected by selective sublimation of said solid concentrated aqueous solution.

43. The process of claim 42 wherein water is removed from said concentrated aqueous solution that has been selectively sublimated, prior to recovery of the solid solute that has been sublimated.

44. The process of claim 43 wherein water is removed by passing said concentrated aqueous solution that has been sublimated over a dehydrating agent.

45. The process of claim 44 wherein the dehydrating agent is anhydrous silica gel.

46. The process of claim 42 wherein the solute is solid acetic acid.

47. The process of claim 1 wherein the aqueous solution comprises vinegar.

48. The process of claim 47 wherein the hydrate forming fluid is trichlorofluoromethane.

49. The process of claim 47 wherein the vinegar is selected from spirit vinegar, grain vinegar, wine vinegar, cider vinegar and a flavoured vinegar.

50. The process of claim 47 wherein the vinegar is malt vinegar.

51. The process of claim 46 wherein the final concentration is at least 80% w/v.

52. The process of claim 47 wherein the concentration process is carried out at least twice on the vinegar to be concentrated.

* * * * *